United States Patent
Copf, Jr. et al.

(10) Patent No.: US 8,460,380 B2
(45) Date of Patent: Jun. 11, 2013

(54) INTERVERTEBRAL IMPLANT AND SURGICAL METHOD FOR SPONDYLODESIS OF A LUMBAR VERTEBRAL COLUMN

(75) Inventors: Franz Copf, Jr., Stuttgart (DE); Wolfhard Pinkowski, Aschheim (DE)

(73) Assignee: Franz Copf, Jr., Stuttgart (DE)

( * ) Notice: Subject to any disclaimer, the term of this patent is extended or adjusted under 35 U.S.C. 154(b) by 1224 days.

(21) Appl. No.: 11/500,707

(22) Filed: Aug. 8, 2006

(65) Prior Publication Data
US 2007/0055374 A1    Mar. 8, 2007

Related U.S. Application Data

(63) Continuation-in-part of application No. PCT/EP2004/001359, filed on Feb. 13, 2005.

(51) Int. Cl.
*A61F 2/44* (2006.01)
(52) U.S. Cl.
USPC ........................................ 623/17.11
(58) Field of Classification Search
USPC ............... 623/17.11–17.16; 606/60, 246–279
See application file for complete search history.

(56) References Cited

U.S. PATENT DOCUMENTS

| | | | |
|---|---|---|---|
| 5,458,638 A | 10/1995 | Kuslich et al. | |
| 5,489,308 A | 2/1996 | Kuslich et al. | |
| 5,683,463 A | 11/1997 | Godefroy et al. | |
| 5,749,916 A | 5/1998 | Richelsoph | |
| 5,766,252 A | 6/1998 | Henry et al. | |
| 5,865,847 A | 2/1999 | Kohrs et al. | |
| 5,885,299 A | 3/1999 | Winslow et al. | |
| 5,888,228 A * | 3/1999 | Knothe et al. | 623/17.16 |
| 5,895,427 A | 4/1999 | Kuslich et al. | |
| 5,897,593 A | 4/1999 | Kohrs et al. | |
| 5,906,616 A * | 5/1999 | Pavlov et al. | 606/247 |
| 5,976,187 A | 11/1999 | Richelsoph | |
| 5,980,522 A * | 11/1999 | Koros et al. | 623/17.11 |
| 6,019,760 A | 2/2000 | Metz-Stavenhagen et al. | |
| 6,033,405 A | 3/2000 | Winslow et al. | |
| 6,059,829 A | 5/2000 | Schlapfer et al. | |
| 6,093,207 A * | 7/2000 | Pisharodi | 623/17.16 |
| 6,120,506 A | 9/2000 | Kohrs et al. | |

(Continued)

FOREIGN PATENT DOCUMENTS

| | | |
|---|---|---|
| DE | 296 00 879 | 3/1996 |
| DE | 297 12 331 | 10/1997 |

(Continued)

OTHER PUBLICATIONS

PCT International Search Report dated Aug. 5, 2004.

*Primary Examiner* — Kevin T Truong
*Assistant Examiner* — Christopher Beccia
(74) *Attorney, Agent, or Firm* — Lempia Summerfield Katz LLC

(57) ABSTRACT

An intervertebral implant has a head positioned at one end of the implant. The head has a conical portion, on which an external thread is formed, and an outer end region formed by a protective elevation. The elevation is, is viewed from the outside, convexly curved and free from sharp edges. A central portion is positioned between the head and a basic structure which is formed at an opposite end of the implant. The central portion is formed by a plurality of struts extending from the head to the basic structure. The central portion is provided with an external thread and has openings formed between the head, the struts and the basic structure.

26 Claims, 4 Drawing Sheets

U.S. PATENT DOCUMENTS

| | | | | |
|---|---|---|---|---|
| 6,129,763 | A | 10/2000 | Chauvin et al. | |
| 6,149,686 | A | 11/2000 | Kuslich et al. | |
| 6,165,219 | A | 12/2000 | Kohrs et al. | |
| 6,168,631 | B1 | 1/2001 | Maxwell et al. | |
| 6,179,873 | B1 | 1/2001 | Zientek | |
| 6,210,412 | B1 | 4/2001 | Michelson | |
| 6,210,442 | B1 | 4/2001 | Wing et al. | |
| 6,287,343 | B1 | 9/2001 | Kuslich et al. | |
| 6,290,724 | B1 * | 9/2001 | Marino | 623/17.11 |
| 6,371,989 | B1 | 4/2002 | Chauvin et al. | |
| 6,391,058 | B1 | 5/2002 | Kuslich et al. | |
| 6,436,140 | B1 | 8/2002 | Liu et al. | |
| 6,447,545 | B1 | 9/2002 | Bagby | |
| 6,527,773 | B1 | 3/2003 | Lin et al. | |
| 6,562,039 | B1 * | 5/2003 | Wang et al. | 606/247 |
| 6,613,091 | B1 * | 9/2003 | Zdeblick et al. | 623/17.16 |
| 6,726,722 | B2 * | 4/2004 | Walkenhorst et al. | 623/17.16 |
| 6,730,125 | B1 * | 5/2004 | Lin | 623/17.11 |
| 6,733,504 | B2 | 5/2004 | Lin et al. | |
| 6,740,091 | B2 | 5/2004 | Kohrs et al. | |
| 6,855,166 | B2 * | 2/2005 | Kohrs | 623/17.11 |
| 6,923,810 | B1 * | 8/2005 | Michelson | 606/247 |
| 6,923,830 | B2 * | 8/2005 | Michelson | 623/17.16 |
| 7,220,280 | B2 | 5/2007 | Kast et al. | |
| 7,267,689 | B2 * | 9/2007 | Kohrs et al. | 623/17.11 |
| 7,291,149 | B1 | 11/2007 | Michelson | |
| 7,331,996 | B2 * | 2/2008 | Sato et al. | 623/17.16 |
| 7,400,930 | B2 * | 7/2008 | Sharkey et al. | 607/117 |
| 7,431,735 | B2 | 10/2008 | Liu et al. | |
| 7,608,105 | B2 * | 10/2009 | Pavlov et al. | 623/17.11 |
| 7,655,046 | B2 * | 2/2010 | Dryer et al. | 623/17.15 |
| 2002/0183846 | A1 * | 12/2002 | Kuslich et al. | 623/17.11 |
| 2002/0193881 | A1 * | 12/2002 | Shapiro et al. | 623/17.11 |
| 2003/0009222 | A1 | 1/2003 | Fruh et al. | |
| 2003/0045938 | A1 * | 3/2003 | Kohrs et al. | 623/17.11 |
| 2003/0171813 | A1 * | 9/2003 | Kiester | 623/17.11 |
| 2004/0127993 | A1 | 7/2004 | Kast et al. | |
| 2004/0267365 | A1 | 12/2004 | Fornari | |
| 2005/0165399 | A1 | 7/2005 | Michelson | |
| 2005/0165489 | A1 | 7/2005 | Michelson | |
| 2006/0085067 | A1 | 4/2006 | Gradel et al. | |
| 2006/0116767 | A1 * | 6/2006 | Magerl et al. | 623/17.12 |
| 2006/0195190 | A1 | 8/2006 | Lechman et al. | |
| 2007/0055374 | A1 | 3/2007 | Copf et al. | |
| 2007/0267365 | A1 | 11/2007 | Saito | |
| 2008/0133015 | A1 | 6/2008 | Lechman et al. | |

FOREIGN PATENT DOCUMENTS

| | | |
|---|---|---|
| DE | 200 12 236 | 10/2000 |
| DE | 199 57 339 C2 | 6/2001 |
| DE | 200 04 692 | 7/2001 |
| EP | 0 758 874 | 3/1995 |
| EP | 0 637 440 | 10/1997 |
| EP | 0 853 932 | 7/1998 |
| EP | 1 103 235 A | 5/2001 |
| EP | 0 844 856 | 10/2001 |
| EP | 0 781 113 | 3/2002 |
| EP | 0 716 840 | 5/2002 |
| EP | 0 784 967 | 11/2002 |
| EP | 1 265 561 | 12/2002 |
| EP | 1 175 878 | 3/2003 |
| EP | 1 290 985 | 3/2003 |
| EP | 0 912 147 | 6/2003 |
| EP | 1 326 559 | 7/2003 |
| EP | 0 831 759 | 3/2004 |
| EP | 1 400 221 | 3/2004 |
| EP | 1 415 623 | 5/2004 |
| EP | 1 014 899 | 8/2004 |
| EP | 0 836 457 | 9/2004 |
| EP | 1 011 481 | 10/2004 |
| EP | 1 107 711 | 10/2004 |
| EP | 1 525 863 | 4/2005 |
| EP | 1 415 622 | 7/2005 |
| EP | 1 635 743 | 3/2006 |
| EP | 1 408 891 | 10/2006 |
| EP | 1 713 421 | 10/2006 |
| EP | 1 740 129 | 1/2007 |
| EP | 1 585 466 | 8/2007 |
| EP | 1 442 732 | 9/2007 |
| EP | 1 148 849 | 12/2007 |
| EP | 1 889 587 | 2/2008 |
| FR | 2 729 557 | 1/1995 |
| FR | 2 710 519 | 4/1995 |
| FR | 2 736 538 | 1/1997 |
| FR | 2 753 368 | 3/1998 |
| FR | 2 760 355 | 9/1998 |
| FR | 2 764 795 | 12/1998 |
| FR | 2 789 297 | 2/1999 |
| FR | 2 841 124 | 6/2002 |
| FR | 2 848 414 | 6/2004 |
| FR | 2 870 449 | 11/2005 |
| FR | 2 920 665 | 3/2009 |
| GB | 2 345 639 | 7/2000 |
| JP | 2001 238891 A | 9/2001 |
| WO | WO 95/25487 | 9/1995 |
| WO | WO 96/22747 | 8/1996 |
| WO | WO 96/27348 | 9/1996 |
| WO | WO 2004/000176 | 12/2003 |

\* cited by examiner

INTERVERTEBRAL IMPLANT AND SURGICAL METHOD FOR SPONDYLODESIS OF A LUMBAR VERTEBRAL COLUMN

CROSS-REFERENCE TO RELATED APPLICATIONS

This is a continuation-in-part of International Patent Application PCT/EP2004/001359, which was filed on Feb. 13, 2005. The full disclosure of this earlier application is incorporated herein by reference.

BACKGROUND OF THE INVENTION

The invention relates to an intervertebral implant and to a method for spondylodesis of the lumbar vertebral column.

German Patent No. DE 199 57 339 C2 describes an intervertebral implant comprising a head which has a conical portion with an external thread, a central portion with an external thread, and a basic structure. The central portion is formed by a plurality of struts extending from the head to the basic structure, and thus large-area windows remain open between the head, the strut and the basic structure.

This known implant deliberately dispenses with the previously known sleeve-type form of intervertebral implants and instead uses a central portion with narrow struts which leave open an optimally large window. A large-area direct path from one vertebral body to another can be exposed in this manner for the spongiosa introduced into the intervertebral implant, and this allows a particularly good frictional connection and accelerates bone formation. In addition X-ray examination during and after an operation is more easily possible with intervertebral implants of this type.

With this known intervertebral implant the head comprises a cylindrical portion, which carries the external thread, and a conical, thread-free portion adjoining at the end region. With this known intervertebral implant it is a risk to carry out a complete distraction, in particular of the ventral circumference of the vertebral body. This is because there is some danger to damage the adjacent vena cava and the aorta.

SUMMARY OF THE INVENTION

It is therefore an object of the present invention to provide an intervertebral implant that it is also suitable for distracting the vertebrae, in particular in the ventral region of the vertebral body.

According to the invention this object is achieved by an implant comprising a head which carries a conical portion and an external thread, a central portion formed on the head and which also carries an external thread, and a basic structure formed on the central portion. The central portion is formed by a plurality of struts extending from the head to the basic structure, so that large-area windows remain open between the head, the strut and the basic structure. The external thread of the head is formed on the conical portion, and the outer end region of the head is formed by a protective elevation which is convexly curved, viewed from the outside, and is free from sharp edges.

Using the external thread of its head the intervertebral implant according to the invention can be screwed into the compacta at the ventral circumference of the vertebral body, wherein, owing to the conicality, a corresponding distraction of the vertebral body takes place. If the protective elevation of the head is in the process moved beyond the ventral edge of the vertebral body, the risk of injuring the adjacent large vessels is reduced owing to its freedom from sharp edges. Rather, if necessary, the protective elevation edges the vessels away slightly from the vertebral bodies in a blunt manner. The intervertebral implant according to the invention may be exactly positioned on the edges of the vertebral body.

The conical portion of the head may have an axial extension of at least 7 mm in order to be able to adequately transmit forces to the vertebral body at the ventral circumference thereof during the distraction procedure.

For the same reason it is expedient for the external thread on the head to comprise at least three full turns.

The protective elevation of the head may have an axial extension of at least 5 mm.

The protective elevation can have the form of a closed cap, or it may be annular with a central through-opening. The through-opening may be provided with an internal thread having a pitch that is oppositely inclined in comparison to the pitch of the external thread of the conical portion. This makes it possible to screw in an extractor instrument in those cases in which the intervertebral cage has to be removed after the implant surgery. This might be necessary, for example, if the intervertebral implant has not fused with the adjacent vertebral bodies.

The basic structure of the intervertebral implant according to the invention may have an axial extension of at least 5 mm. This takes account of the anatomical fact that the compacta at the dorsal side of the vertebral body is thinner than at the ventral side.

The basic structure, which may be formed as a plate, may comprise an application device for a screw-in instrument. It may be coupled to the screw-in instrument merely with positive action of the surgeon and may likewise be released again merely with active involvement of the surgeon. Application devices of this type are known as such.

The angle enclosed by the conical circumferential surface of the conical portion of the head and by an imaginary coaxial circumferential surface of a circular cylinder may be between 10° and 20°, and preferably be 15°, largely independently of the individual patient data.

A particularly advantageous embodiment of the intervertebral implant according to the invention is characterised in that the central portion and the basic structure are conical in the opposite direction to the conical portion of the head. The conicality of the central portion and the basic structure thus determine the lordosis of the two vertebral bodies between which the intervertebral implant is inserted.

According to the general anatomical conditions it is usually sufficient if two coning angles are optionally held ready for the central portion and the basic structure: the angle enclosed by the conical circumferential surface of the central portion and the basic structure and by an imaginary coaxial circumferential surface of a circular cylinder may be about 3° in one embodiment and in another embodiment be about 6°.

The intervertebral implant can be made of different materials, in particular of stainless steel, carbon-ceramic material, aluminium alloys, titanium, plastics material, in particular polyisocyanate or the like.

The intervertebral implant according to the invention can, however, also be produced from bioresorbable material, in particular polyactide.

If the intervertebral implant has a non-rotationally symmetrical cross-sectional shape in at least one axial region, it is secured against unintentional rotation after screwing-in. It is particularly advantageous here if the basic structure itself, which cooperates with the dorsal region of the compacta of the vertebral bodies, has non-rotationally symmetrical cross-sectional shape.

The intervertebral implant is particularly gentle for the vessels if its protective elevation is polished.

According to the present invention, a surgical method is provided which is gentle for the patient for spondylodesis of the lumbar vertebral column. The method comprises the following steps:
 a) access to the intervertebral space is opened microsurgically from the dorsal side and with partial removal of the small vertebral joints;
 b) the cartilage fractions of the deck plate and basal plate of the intervertebral space are removed;
 c) a thread is cut into the dorsal region of the intervertebral space;
 d) the intervertebral space is pre-distracted using a distraction instrument;
 e) the pre-distraction is maintained using a spacer and the distraction instrument is removed;
 f) a first intervertebral implant is screwed into the thread in the intervertebral space;
 g) steps a) to f) are repeated for a second intervertebral implant which is inserted at a spacing from the first intervertebral implant.

This new method spares the patient owing to is microsurgical configuration and its application from the dorsal side, and causes only small wounds. The risk of infection is therefore considerably reduced. The patient is exposed to much less pain, and the time spent in hospital is considerably shorter.

If the patient has not already been pre-operated on, it may be necessary after step a) to thin out the Ligamentum flavum from the outside to the inside. An inner region is retained in the process however, so scar formation is largely avoided.

After step b) the exposed bone fractions can be freshened, in other words superficially abraded, and this facilitates adherence with spongiosa introduced into the intervertebral space.

The intervertebral implants themselves should be filled with spongiosa before introduction into the intervertebral space.

The intervertebral space itself is also preferably filled with spongiosa at the latest before introduction of the second intervertebral implant.

The method according to the invention is particularly helpful if the new intervertebral implant is used which has been described above. This implant is then screwed in with distraction, in particular of the ventral region, until the transition line between the protective elevation and the conical region of the head is at the height of the apexes in the lateral image of the ventral circumference of the vertebral bodies. With this configuration of the method according to the invention, the ventral region of the vertebral body in particular may therefore also be distracted in the required manner without risk.

When screwing-in the intervertebral implant the torque may be measured. If a predetermined value of the torque is fallen below this means that the maximum diameter of the intervertebral implant used is too small and the distraction achieved is not sufficient. A different intervertebral implant with a larger maximum diameter is then selected.

BRIEF DESCRIPTION OF THE DRAWINGS

Various features and advantages of the present invention may be more readily understood with reference to the following detailed description taken in conjunction with the accompanying drawing in which.

DESCRIPTION OF PREFERRED EMBODIMENTS

Figure 1:
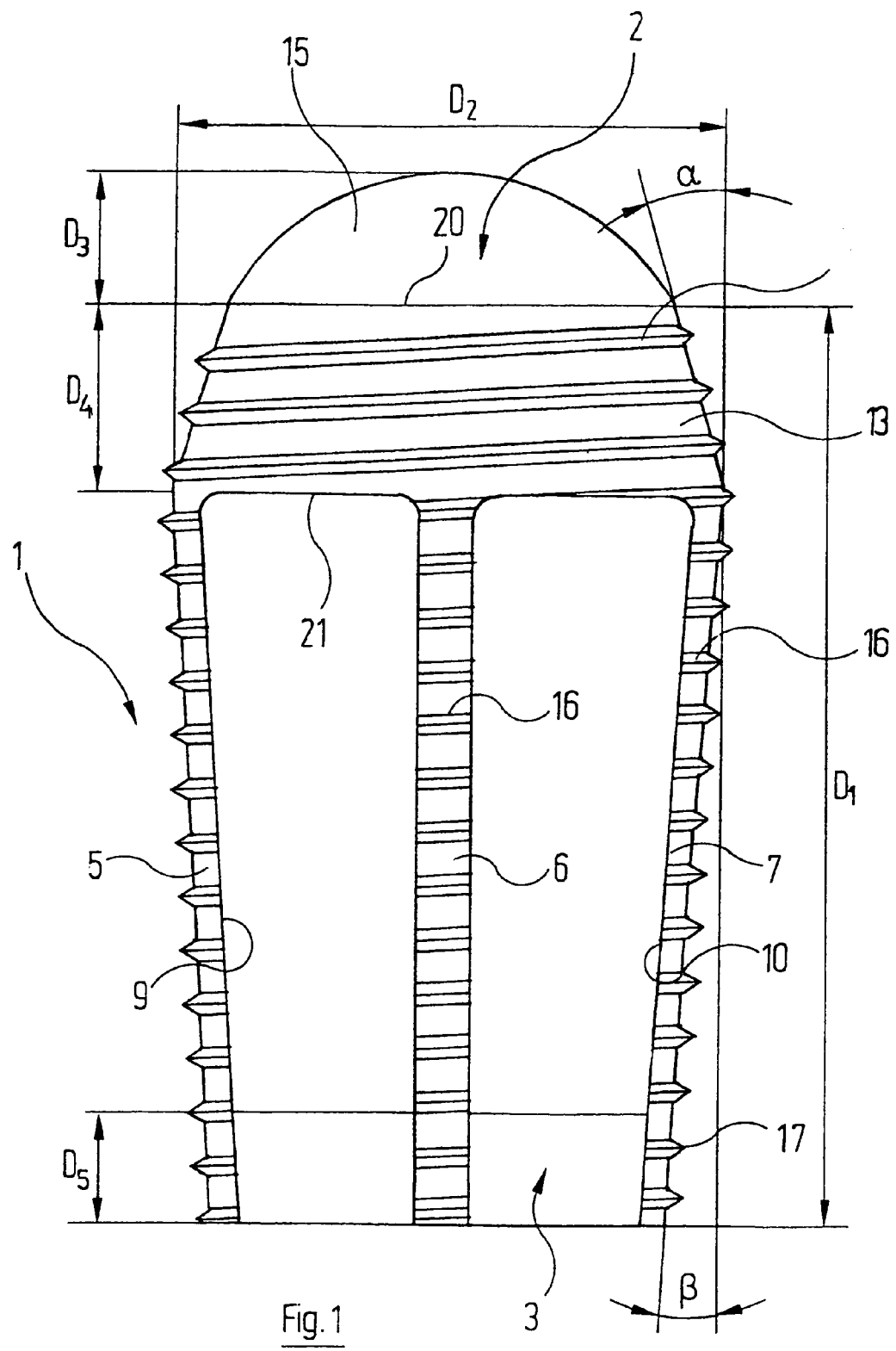
FIG. 1 shows an intervertebral implant in a side view according to a first embodiment of the invention.

Reference will firstly be made to FIG. 1 which shows an intervertebral implant designated in its entirety by reference numeral 1. The implant comprises an (in the implanted state) ventrally-pointing head 2 and an (in the implanted state) dorsally-pointing base plate 3 which are connected to each other by four narrow struts 5, 6, 7 and 8. Large-area windows 9, 10, 11, 12 remain between the struts 5, 6, 7, 8, the head 2 and the base plate 3.

The head 2 of the intervertebral implant 1 comprises a conical portion 13, which carries an external thread 14, and a, viewed from the outside, convex protective cap 15 adjoining the conical portion 13 and forming the ventral end of the intervertebral implant 1. The protective cap 15, which has a spherical cap surface in the embodiment shown, is polished for reasons which will be elucidated below. In particular, the cap 15 does not have any sharp edges. The arrow height $D_3$ of the protective cap 15 is at least 4 to 5 mm. The reason for this will also become clear below. The conical portion 13 has an axial length $D_4$ which should not fall below 7 mm. The external thread 14 has at least three full turns inside the conical portion 13. The angle α which the circumferential surface of the cone of the conical portion 13 encloses with an imaginary circumferential surface of a circular cylinder and which corresponds to half the cone angle is between 10° and 20°, preferably about 15°.

The struts 5, 6, 7, 8 are also located on an imaginary surface of a circular cone which tapers in the opposite direction to the conical region 13 of the head 2 toward the dorsal end of the intervertebral implant 1, located at the bottom in FIG. 1. The angle β which the circumferential surface of this imaginary cone encloses with a circumferential surface of a circular cylinder and which corresponds to half the cone angle is about 6° or about 3°, depending on between which vertebral bodies the intervertebral implant 1 is to be inserted. The struts 5, 6, 7, 8 also carry an external thread 16 which is constructed as a continuation of the external thread 14 on the conical region 13 of the head 2.

Figure 2:
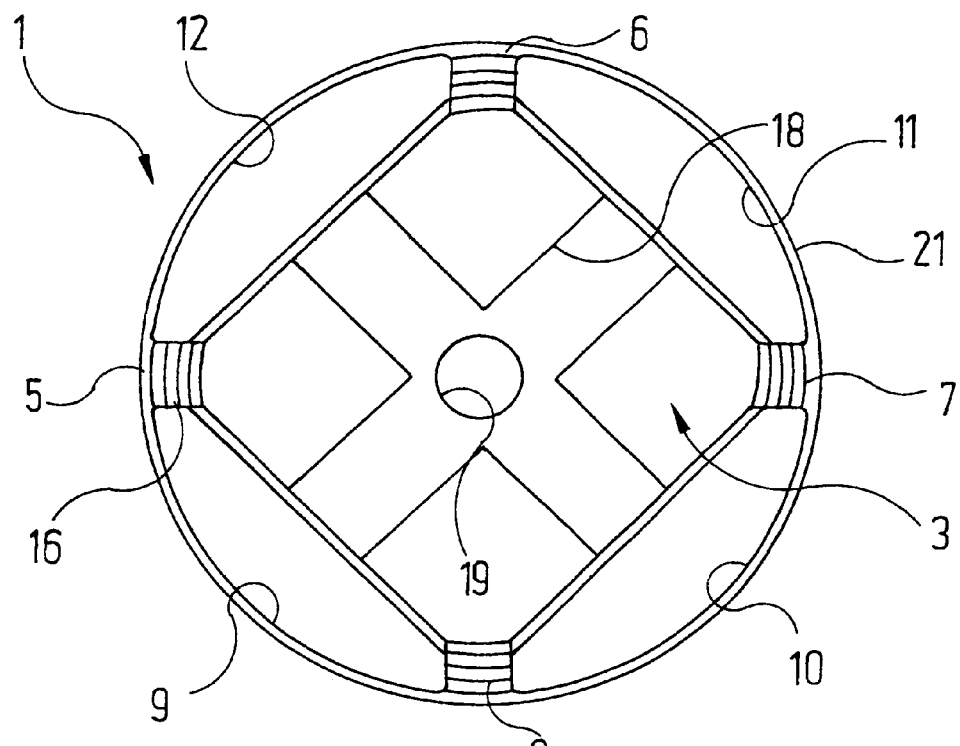
FIG. 2 is a bottom view of the intervertebral implant shown in FIG. 1.

The struts 5, 6, 7, 8 merge in one piece into the rounded corners of the base plate 3, as becomes particularly clear from FIG. 2. The bottom view of the base plate 3 is approximately square. The external thread 16 of the struts 5, 6, 7, 8 continues in an external thread 17 on the rounded corners of the base plate 3.

An application device for a screw-in instrument is worked into the lower side of the base plate 3, as can be seen in FIG. 2. In this embodiment the application device has the form of a cross groove 18. The associated screw-in instrument, which is not shown in the drawings, has a complementary cross-shaped axially extending projection and can be clicked into a latching device 19 which is schematically shown in the drawings as a circular hole. The latching device 19 is configured in such a way that the production of a connection between the screw-in instrument and the cross-groove 18 requires a positive action by the surgeon, and conversely release of the screw-in instrument from the base plate 3 can only take place with positive action by the surgeon and not unintentionally. Connections of this type are known per se and individually and so do not need to be described in more detail here.

The axial extension $D_5$ of the base plate 3 should not fall below 4 mm.

Figure 4:
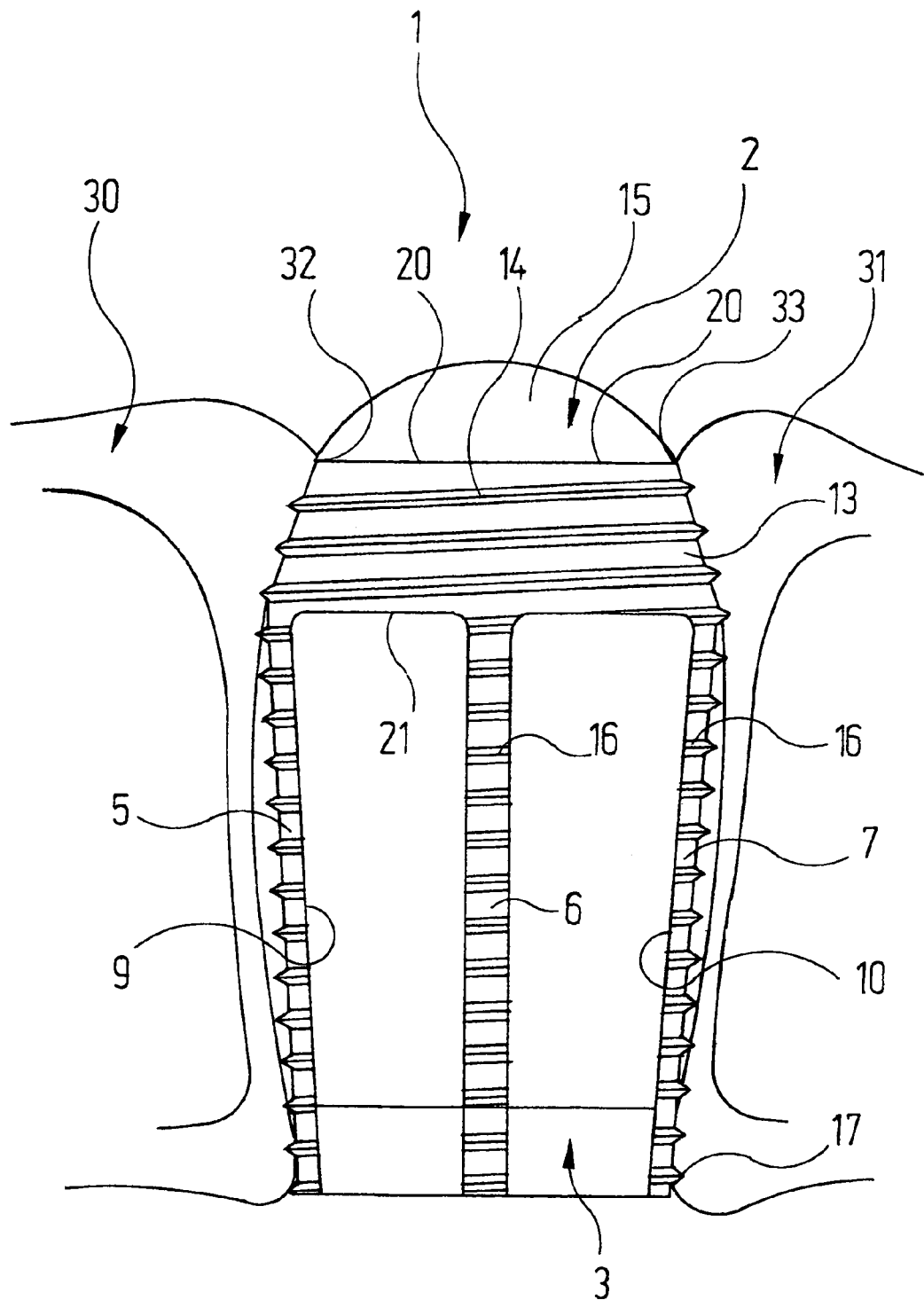
FIG. 4 shows on a slightly larger scale and in a side view an intervertebral implant between two vertebral bodies illustrated in section.

As described thus far the intervertebral implant 1 does not substantially differ from patient to patient. Individual patient information flows into the dimensions of the intervertebral implant 1 in the following manner, however and must be taken preoperatively from CT scans or X-ray images:

The axial distance $D_1$ between the dorsal, outer end face of the base plate 3 and the transition line 20 between the conical region 13 of the head 2 and the polished protective cap 15 corresponds, as may be gathered in particular from FIG. 4, to the spacing between the dorsal outer edges of the vertebral bodies 30, 31 to be connected and the opposing vertices 32, 33 of the ventral edges of the vertebral bodies 30, 31 in the lateral image. The implantation position of the intervertebral implant 1 is therefore such that the dorsal outer end face approximately aligns with the dorsal edges of the vertebral bodies 30, 31 while the transition line 20 at the head 2 of the intervertebral implant 1 connects the vertices 32, 33 of the two vertebral bodies 30, 31. The protective cap 15 of the head 2 projects in the process ventrally beyond the ventral edges of the vertebral bodies 30, 31.

The intervertebral implant 1 can be made of different materials. On the one hand, as already described in the above-mentioned DE 199 57 339 C2, stainless steel or carbon-ceramic material may be considered. As a permanent material that remains in the body aluminium alloys, titanium and certain plastics materials, in particular polyisocyanate (PIC), are also suitable. Bioresorbable materials, such as polyactide in particular, in other words co-polymers of poly (L-lactide-co-D, L-lactide), as sold for example under the trade name Telamon®, may also be used, however.

Sets of intervertebral implants 1 which differ in terms of the size of the dimension D1 therefore have to be held ready for different patients. In general it is sufficient to provide gradations of 2 mm here, wherein in practice dimensions D1 of 28, 30, 32, 34 and 36 mm can be considered in particular.

The largest diameter D2 of the intervertebral implant 1 occurs, as becomes clear from the above description, at the transition line 21 between the head 2 and the struts 5, 6, 7. It corresponds to the desired distraction between the adjacent vertebral bodies 30, 31 and can be taken from the X-ray image, for example from neighbouring healthy segments. A whole set of intervertebral implants 1 which have to be kept ready by the surgeon is thus required with respect to dimension $D_2$ as well. A gradation of 2 mm is again sufficient. In practice dimensions $D_2$ of primarily 10, 12, 14 and 16 mm are considered.

In the case of an embodiment of the intervertebral implant 1 not shown in the drawings the ventral end is not formed by a closed protective cap. Instead, the cap is replaced by a ring that has an opening and is convexly curved if viewed from the outside. The opening should not be larger than 5 mm. The outer face of such a protective ring pointing in the ventral direction should also be polished.

The surgeon carries out spondylodesis using the described intervertebral implant 1, of which two are required in each case, as follows:

Firstly the individual items of information $D_1$ and $D_2$ of the intervertebral implants 1 to be used are determined preoperatively from the CT scans or X-ray images. The angle β is selected according to the desired lordosis of the vertebral bodies that are to be joined together.

The operation is carried out by way of microsurgery from the dorsal side. The required access to the intervertebral space is obtained by partial removal of the small vertebral joints, wherein the Ligamentum flavum can largely be spared in the case of patients that have not been operated on already. This merely needs to be thinned out slightly from the outside to the inside, so that an inner layer is retained. Scar formation is thus avoided.

The intervertebral space is then carefully freed from cartilage fractions of the deck plate and basal plate. The bone fractions are "freshened" in the process, i.e. thinly superficially abraded, wherein their load-bearing capacity is not damaged. A pre-distraction of the vertebral bodies 30, 31 is then carried out using a distraction instrument which substantially attaches at the dorsal vertebral edges. The pre-distraction thus achieved is maintained by a sleeve provided with two attached spacer clips introduced into the intervertebral space when the distraction instrument is now removed again.

A thread is then cut through this sleeve in the dorsal part of the intervertebral space. A first intervertebral implant 1 is now introduced through the sleeve head 2 first and by rotation screwed to the thread of the vertebral body 30, 31 cut-in in advance, so that it moves axially in the ventral direction. The intervertebral implant 1 has been filled with spongiosa in advance.

The intervertebral implant 1 is now rotated until the external thread 14 on the head 2 of the intervertebral implant 1 comes to rest against the compacta of the ventral circumference of the two vertebral bodies 30, 31. With further rotation of the intervertebral implant 1 the external thread 14 cuts into the compacta of the ventral edges of the vertebral body 30, 31, wherein the conical shape of the conical region 13 of the head 2 provides a corresponding distraction of the ventral edges of the vertebral bodies 30, 31. The screwing-in movement of the intervertebral implant 1 is continued with X-ray observation until the transition line 20 comes to rest in the region of the vertices 32, 33 of the two vertebral bodies 30, 31. Further movement cannot take place. Up to this point the protective cap 15 of the head 2 may have pushed away the vena cava and the aorta, which extend in this direction, slightly in the ventral direction. However, the risk of injuring these vessels is small as the protective cap does not have any sharp edges.

Figure 3:
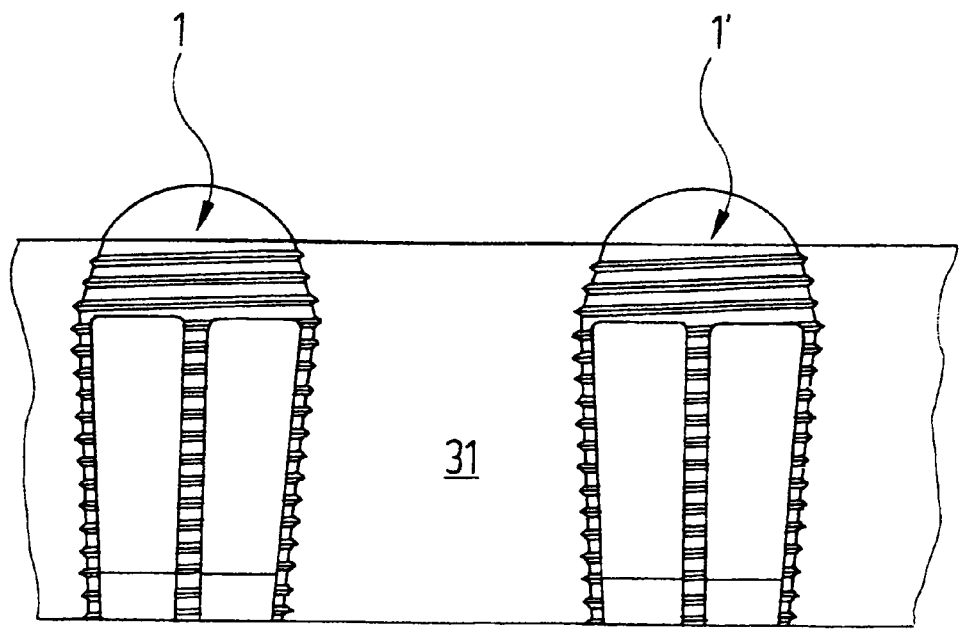
FIG. 3 schematically shows in a plan view two intervertebral implants implanted side by side between two vertebral bodies.

The remaining intervertebral space is now filled with spongiosa and a second intervertebral implant 1' inserted next to the first intervertebral implant 1 in the above-described manner (cf. FIG. 3). The spacing between the two intervertebral implants 1, 1' should not be less than 1 cm. The second intervertebral implant 1' has also already been filled with spongiosa before insertion.

When screwing-in the external thread 14 of the two intervertebral implants 1, 1' the torque that is required for this is measured. If this torque is below a specific value this is an indication of the fact that the dimension $D_2$ of the intervertebral implant 1 selected from the set is too small. The intervertebral implant 1 must then be exchanged for one whose dimension D2 is slightly larger.

With sufficient distraction without ventral displacement of the vertebral body no further measures are required. A "stand alone" technique is therefore sufficient in this case in which only the intervertebral implants 1, 1' are inserted. Otherwise additional securing by means of a fixateur interne takes place.

Figure 5:
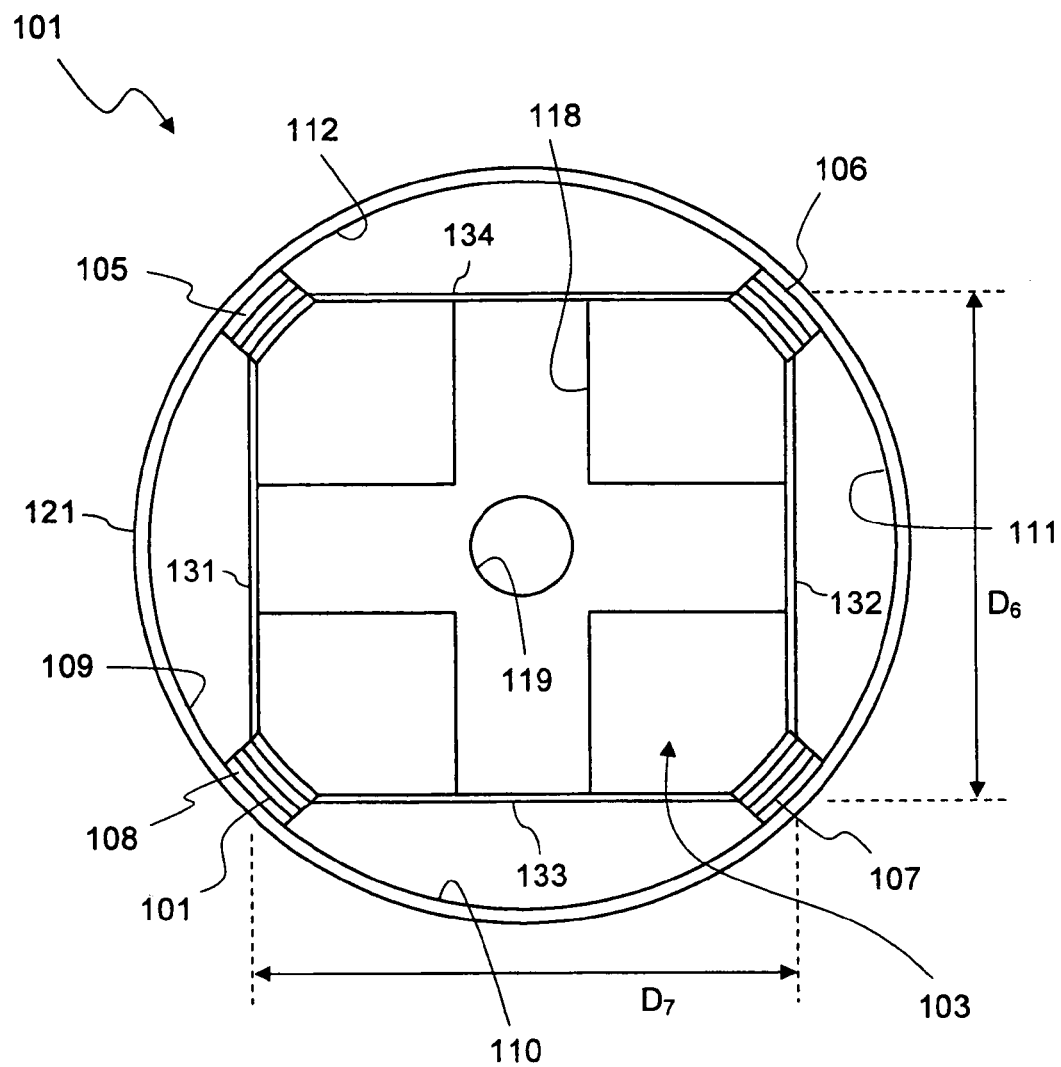
FIG. 5 is a bottom view of an intervertebral implant according to a second embodiment of the invention.

FIG. 5 is a bottom view similar to FIG. 2 of an intervertebral implant according to another embodiment of the invention. For parts corresponding to the previous embodiment reference numerals augmented by 100 are used.

The intervertebral implant 101 shown in FIG. 5 differs from the intervertebral implant 1 shown in FIGS. 1 to 4 only in that the base plate 103 is not square, but has a rectangular base geometry. The shorter lateral sides 131, 132 have a lengths $D_6$, and the longer lateral sides 133, 134 have a length $D_7 > D_6$. The head of the intervertebral implant 101 has still a circular cross section. As a result, the struts 105, 106, 107, 108 connecting the rotationally symmetric head with the rotationally asymmetric base plate 103 form different angles β in two orthogonal planes. More specifically, the angle β in one axial plane that vertically intersects the plane of the sheet is smaller than the angle β in a plane orthogonal thereto, i.e. in a plane intersecting the plane of the sheet horizontally.

The selection of the angle β which finally becomes effective in that it determines the lordosis, depends on the angular orientation which the intervertebral implant 101 has in the intervertebral space after its insertion. For example, the lengths $D_6$ and $D_7$ of the sides 131, 132 and 133, 134 of the base plate 103 could be selected such that a first angle $β_1 = 3°$ is obtained in a first plane, and a second angle $β_2 = 6°$ is obtained in a second plane which is orthogonal to the first plane. The larger the aspect ratio between the sides 131, 132 on the one hand and the sides 133, 134 on the other hand is, the larger is the difference between the first and second angles $β_1$, $β_2$.

As can be seen best in FIG. 4 for the intervertebral implant 1, the lordosis is, strictly speaking, not determined by the inclined struts 5, 6, 7, 8, but by the difference between the largest diameter of the head 2 and the diameter of the base plate 3. This is because not the inclined struts 5, 6, 7, 8, but only the head 2 and the base plate 3 are usually in direct contact with the adjacent vertebral bodies.

For the intervertebral implant 101 this implies that the two-fold rotational symmetry of the base plate 103 is mainly responsible for the different lordosis that may be obtained with the implant 103 in different angular positions.

Since it is possible with one single intervertebral implant 101 to select from two different angles $β_1$, $β_2$, the overall number of intervertebral implants required for covering all possible geometric configurations is reduced by a factor 2.

In the embodiment shown the grooves of the cross groove 118 have different lengths, too, and thus the cross groove does not have a fourfold, but only a twofold symmetry. The screw-in instrument, which is not shown in the drawings, has a complementary cross-shaped axially extending projection with a twofold symmetry. This ensures that this instrument can be attached to the base plate 103 only in two different angular orientations. If the instrument is provided with an appropriate marking on its shaft, the surgeon can see with the help of the marking in which angular orientation the intervertebral implant 101 is positioned within the intervertebral space. For example, if the surgeon desires to obtain the first angle $β_1$, he rotates the instruments until the marking indicates the correct position. If the surgeon desires to obtain the second angle $β_2$, he simply rotates the instrument by 90°.

Since the head has preferably a circular cross section, the provision of two different angles $β_1$, $β_2$ does not impede the screwing-in of the intervertebral implant 101 into the intervertebral space. If the vertebral bodies 30, 31 are pre-distracted by a sleeve as has been explained above, the screwing-in operation of the rotationally asymmetric central portion and base plate 103 are not impeded by the vertebral bodies 30, 31. After removal of the sleeve the vertebral bodies 30, 31 will rest on the struts 105, 106, 107, 108 with the angle β selected by the angular orientation of the intervertebral implant 103.

As a matter of course, the above described second embodiment may be varied in various ways. For example, the base plate 103 as such may be rotationally symmetrical or may still have fourfold symmetry, but the struts 105, 106, 107, 108 are connected to the base structure 103 such that nevertheless different angels $β_1$, $β_2$ are obtained in two orthogonal planes, or the struts 105, 106, 107, 108 are curved in different ways. It may also be envisioned to have three different angles $β_1$, $β_2$, $β_3$ that may be selected by rotating the implant by angles of 60°. A base plate having a hexagonal base geometry may be used in this context.

The above description of the preferred embodiments has been given by way of example. From the disclosure given, those skilled in the art will not only understand the present invention and its attendant advantages, but will also find apparent various changes and modifications to the structures and methods disclosed. The applicant seeks, therefore, to cover all such changes and modifications as fall within the spirit and scope of the invention, as defined by the appended claims, and equivalents thereof

What is claimed is:

1. An intervertebral implant, comprising:
    a) a head positioned at one end of the implant, said head comprising a conical portion on which an external thread is formed and which is free of openings, and an outer end region formed by a protective elevation which is, if viewed from the outside, convexly curved and free from sharp edges,
    b) a basic structure formed at an opposite end of the implant, and
    c) a central portion positioned between the head and the basic structure, wherein said central portion is formed by a plurality of struts extending from the head to the basic structure, has an axial length greater than the head and the basic structure, has openings formed between the head, the struts and the basic structure, the openings extending lengthwise from the conical portion of the head to the basic structure, the openings having lengthwise ends terminating in the central portion not in the conical portion of the head, and has an external thread.

2. The implant of claim 1, wherein the conical portion of the head has an axial extension of at least 7 mm.

3. The implant of claim 1, wherein the external thread on the head comprises at least three full turns.

4. The implant of claim 1, wherein the protective elevation of the body has an axial extension of at least 5 mm.

5. The implant of claim 1, wherein the protective elevation has the form of a closed cap.

6. The implant of claim 1, wherein the protective elevation is annular and has a central opening.

7. The implant of claim 1, wherein the basic structure has an axial extension of at least 5 mm.

8. The implant of claim 1, wherein the basic structure is a plate.

9. The implant of claim 1, comprising on the basic structure an application device for a screw-in instrument.

10. The implant of claim 1, wherein an angle, which is formed between a conical circumferential surface of the conical portion of the head on the one hand and an imaginary coaxial circumferential surface of a circular cylinder on the other hand, is between 10° and 20°.

11. The implant of claim 1, wherein the central portion and the basic structure are conically shaped in a direction opposite to the conical portion of the head.

12. The implant of claim 11, wherein an angle, which is formed between a conical circumferential surface of the central portion and the basic structure on the one hand and an imaginary coaxial circumferential surface of a circular cylinder on the other hand, is about 3°.

13. The implant of claim 11, wherein an angle, which is formed between a conical circumferential surface of the central portion and the basic structure on the one hand and an imaginary coaxial circumferential surface of a circular cylinder on the other hand, is about 6°.

14. The implant of claim 1, which has, in at least one axial region, a non-rotationally symmetrical cross-section.

15. The implant of claim 14, wherein the basic structure has a non-rotationally symmetrical cross-section.

16. The implant of claim 1, wherein the protective elevation is polished.

17. An intervertebral implant, comprising:
a) a head positioned at one end of the implant, said head comprising a conical portion on which an external thread is formed,
b) a basic structure formed at an opposite end of the implant, and
c) a central portion positioned between the head and the basic structure, wherein said central portion is formed by a plurality of struts extending from the head to the basic structure, has openings formed between the head, the struts and the basic structure, and has an external thread, wherein a diameter of the head increases in a direction towards the central portion and the central portion and the basic structure are conically shaped but become smaller in diameter in a direction opposite to the conical portion of the head.

18. An intervertebral implant, comprising:
a) a head positioned at one end of the implant, said head comprising a conical portion on which an external thread is formed, and an outer end region formed by an annular protective elevation which is convexly curved if viewed from the outside, is free from sharp edges, and has a central opening,
b) a basic structure formed at an opposite end of the implant, and
c) a central portion positioned between the head and the basic structure, wherein said central portion is formed by a plurality of struts extending from the head to the basic structure, has openings formed between the head, the struts, and the basic structure, and has an external thread.

19. The implant of claim 18, wherein the central opening of the protective elevation is provided with an internal thread having a pitch that is oppositely inclined in comparison to the pitch of the external thread on the conical portion.

20. The intervertebral implant of claim 17, wherein the external thread on the head comprises at least three full turns.

21. The intervertebral implant of claim 17, wherein the head further comprises an outer end region formed by a protective elevation which is, if viewed from the outside, convexly curved and free from sharp edges, wherein the protective elevation is annular and has a central opening.

22. The intervertebral implant of claim 17, wherein the basic structure has a non-rotationally symmetrical cross-section.

23. An intervertebral implant, comprising:
a) a head positioned at one end of the implant, said head comprising a conical portion on which an external thread is formed,
b) a basic structure formed at an opposite end of the implant, and
c) a central portion positioned between the head and the basic structure, wherein said central portion is formed by a plurality of struts extending from the head to the basic structure, has openings formed between the head, the struts and the basic structure, and has an external thread, wherein the central portion and the basic structure are conically shaped but become smaller in diameter in a direction opposite to the conical portion of the head, and wherein the openings do not extend into the conical portion of the head.

24. The intervertebral implant of claim 23, wherein the external thread on the head comprises at least three full turns.

25. The intervertebral implant of claim 23, wherein the head further comprises an outer end region formed by a protective elevation which is, if viewed from the outside, convexly curved and free from sharp edges, wherein the protective elevation is annular and has a central opening.

26. The intervertebral implant of claim 23, wherein the basic structure has a non-rotationally symmetrical cross-section.

* * * * *